United States Patent [19]

Carazzolo et al.

[11] 4,435,604

[45] Mar. 6, 1984

[54] METHOD FOR THE RECOVERY OF PENTAERYTHRITOL FROM THE RESIDUAL MIXTURES OF THE SYNTHESIS FROM ACETALDEHYDE AND FORMALDEHYDE

[75] Inventors: Gianalvise Carazzolo, Castellanza; Giancarlo Colombo, Milan; Giulio Gavella, Imola; Silvano Giacomuzzo, Cassano Magnago; Franco Gianetti, Gallarate, all of Italy

[73] Assignee: Montedison S.p.A., Milan, Italy

[21] Appl. No.: 379,778

[22] Filed: May 19, 1982

[30] Foreign Application Priority Data

May 22, 1981 [IT] Italy ............................ 21891 A/81

[51] Int. Cl.$^3$ .................. C07C 31/24; C07C 29/88
[52] U.S. Cl. .................... 568/854; 549/352; 549/369; 568/672
[58] Field of Search ........................ 568/854

[56] References Cited

U.S. PATENT DOCUMENTS

| | | | |
|---|---|---|---|
| 2,533,737 | 12/1950 | Mertz | 568/854 |
| 3,076,854 | 2/1963 | Klein | 568/854 |
| 3,097,245 | 7/1963 | Russell et al. | 568/854 |
| 4,083,931 | 4/1978 | Lee | 568/854 |
| 4,105,575 | 8/1978 | Eckler | 568/854 |

FOREIGN PATENT DOCUMENTS

| | | | |
|---|---|---|---|
| 576266 | 5/1959 | Canada | 568/854 |
| 684683 | 4/1964 | Canada | 568/854 |
| 713611 | 7/1965 | Canada | 568/854 |

*Primary Examiner*—J. E. Evans

[57] ABSTRACT

Method for the recovery of pentaerythritol from a residual mixture of the synthesis from acetaldehyde and formaldehyde, said mixture containing, besides other byproducts, greater amounts of formals, said method being characterized by a transacetalization of said formals, realized by contact of the residual mixture with a saturated aliphatic alcohol having from 1 to 4 carbon atoms.

14 Claims, No Drawings

METHOD FOR THE RECOVERY OF PENTAERYTHRITOL FROM THE RESIDUAL MIXTURES OF THE SYNTHESIS FROM ACETALDEHYDE AND FORMALDEHYDE

BACKGROUND OF THE INVENTION

The present invention concerns a method for the recovery of pentaerythritol from residual mixtures resulting from the synthesis of pentaerythritol itself, said residual mixtures containing, together with other by-products, greater amounts of formals.

It is known from Italian Patent Publication 21222 A/78, assigned to Montedison, S.p.A., Milan, Italy, to synthesize pentaerythritol by multiple aldolic condensation of acetaldehyde with formaldehyde and by successive disproportioning, in the presence of aqueous sodium hydroxide. It is also known to crystallize the greatest part of pentaerythritol from the synthesis mother liquor, by then isolating, separately from said mother liquor, a non-negligible amount of pentaerythritol (not previously precipitated), almost stoichiometric quantities of sodium formate and residual mixtures containing (besides minor amounts of pentaerythritol, formate and other byproducts) considerable amounts of formals. Said residual mixtures may be isolated as an alcoholic solution (obtainable, for instance, according to the Italian Patent Publication hereinabove or according to Japanese Patent Publication No. 15 566/77) by means of an extraction of the formals and of the other undesired byproducts from the synthesis mother liquor, using an alcohol as extracting agent. Said Japanese Publication teaches, moreover, to remove the alcohol by means of an evaporation and to hydrolize the formals with an acid, in an aqueous solution.

Operating in this way, the recovery yields are not, however, very great; besides that, the physical separation of the pentaerythritol from the aqueous medium thus obtained proves rather troublesome.

OBJECT OF THE INVENTION

One object of the invention is to avoid the drawbacks hereinabove; still further objects will be more clearly pointed out in the description that follows.

DESCRIPTION OF THE INVENTION

In its more general form, the invention concerns a method for the recovery of pentaerythritol from a residual mixture of the synthesis of pentaerythritol itself, said mixture containing, besides other byproducts, greater amounts of formals. The method is characterized by a transacetalization of said formals, realized by contacting the residual mixture, in a substantially anhydrous medium and in the presence of an acid, with a saturated aliphatic alcohol having from 1 to 4 carbon atoms, at a temperature either equal to or greater than 60° C., but preferably comprised between 70° and 130° C. (between 70° and 100° C. when the alcohol is methanol), whereby one obtains a precipitation both of the pentaerythritol already present in the mixture in the free state, as well as of the pentaerythritol released when the acid is added, according e.g. to the following equation:

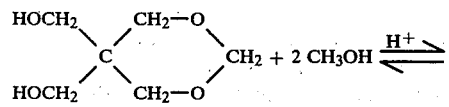

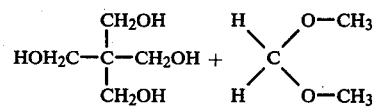

By this method it is possible to recover considerable amounts of the pentaerythritol existing in the residual mixtures, either free or combined, and the recovered pentaerythritol may be separated directly (for instance by filtering or centrifuging) from the transacetalization mixture in which it precipitates, due to its low solubility in alcohols.

A second advantage resides in the concomitant production of the formals of the used alcohols. If the obtained formal boils at a lower temperature than that at which the corresponding alcohol boils, then the formal itself may be easily removed from the raw transacetalization mixture by means of a rectification.

When ethylene or propylene glycols are used as the alcohol, it is possible to obtain also valuable by-products such as respectively 1,3-dioxolane and 1,3-dioxane, and when methanol is used it is possible to obtain methylal, which is advantageously used in different fields of chemistry.

A further advantage resides in the excellent solution of a delicate environmental problem associated with the disposal of the waste residues obtained otherwise.

THE PREFERRED EMBODIMENT

According to one particular form of embodiment, no water at all is added and care is taken that the amount of water in the reaction mixture is equal to or less than 10% but preferably 5% by weight with respect to the residual mixture to be trans-acetalized. The acid should be selected from the group comprising sulphuric acid, phosphoric acid, paratoluene-sulphonic acid and the cation-exchanging resins, and the alcohol should be selected from the group comprising methanol, ethylene glycol and 1,3-propylene glycol. The absence of water is a very important factor inasmuch as too high contents in water would appreciably reduce the transacetalization yield.

It is advisable to feed the acid together with the alcohol and with the residual mixture to be transacetalized into a reactor surmounted by a rectification column; it is thus possible to carry out contemporaneously the transacetalization of the heavy formals and the removal of the volatile formal of the added alcohol, which has formed during the reaction, as well as the other volatile compounds existing in the reaction mixture.

The reaction time must correspond to a satisfactory degree of conversion, but at the same time it must be kept within reasonable limits. In general it has been proved advantageous to keep said time above 15 minutes and preferably between 0.5 and 5 hours.

Finally, it is advantageous to apply by weight ratios:

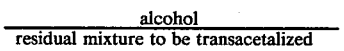

between 0.2 and 3, but preferably between 0.25 and 1. As far as the acid is concerned, if use is made of sulphuric acid it is advisable to use catalytic amounts between 0.5 and 10% by weight with respect to the whole of the reaction mixture; if the acid is a different one, the amounts must be stoichiometrically equivalent. A last detail concerns the pressure which must be such as to keep the mixture (containing the recovered pentaerythritol) in the liquid state, at the prefixed temperature; although it is possible also to operate under vacuum, it would be advisable to keep a pressure between atmospheric pressure and 5 absolute atmospheres. The residual mixtures, object of the invention, contain, in general, besides pentaerythritol and formals, also other compounds as for instance ethers and, in particular, small but not negligible amounts of sodium formate, which may be conveniently removed before the transacetalization, by passing the mixture over ion-exchanging resins. The invention may be applied to said mixtures either before being passed over the resin or after their passage over it, but best results are obtained when the mixtures are pre-treated with said resins.

The examples given hereinbelow illustrate the invention without, however, limiting in any way the scope of the invention itself. More particularly it must be stressed that the invention refers to all residual mixtures containing pentaerythritol formals, however they have been isolated.

EXAMPLE 1

According to the method described in Italian Patent Publication 21,222 A/78, a residual mixture was separated from the mother liquor of a pentaerythritol synthesis, said mixture containing different byproducts and having the composition A reported on Table 1. A second and a third mixture, indicated by letters B and C on Table 1, were obtained by treating the synthesis mother liquor in a slightly different way, and by then pre-treating the mixtures thus obtained with cation-exchanging resins and, in the case of mixture B, also with anion-exchanging resins, whereby we reached the practically total removal of the sodium formate still present.

441 g of the deionized mixture indicated as B on Table 1, were brought into contact with 147 g of methanol, in the presence of 12 g of a 98% by weight sulphuric acid, thereupon bringing this reaction mixture to boiling in a flask fitted with a stirrer and surmounted by a rectification column. The reaction was carried out at room pressure for 2 hours and 50 minutes, with a reflux ratio of 30:1, whereby the temperature in the flask passed from 75° to 91° C., while the temperature in the head of the rectification column passed from 41° to 58.5° C. At the end were obtained 109 g of a head-distillate containing (% by weight):

| H$_2$O | 0.1% | CH$_3$O—CH$_2$—OCH$_3$ | 62.35% |
|---|---|---|---|
| CH$_3$—O—CH$_3$ | 0.15% | CH$_3$OH | 37.45% |
| HCOO—CH$_3$ | 0.05% | | |

The residual bottoms in the flask were then cooled down to room temperature and suspended for about half an hour in 190 grams of methanol, whereafter they were filtered under pressure and the crystals thereby obtained were washed with further 170 grams of methanol. After drying in a suitable oven, we obtained 221 g of crystals containing 95.5% by weight of pentaerythritol, which corresponds to 47.9 g of PE for each 100 g of starting mixture B (de-ionized mixture). Originally the free pentaerythritol was equal only to $$20.6 \times \frac{97.3}{100} = 20 \text{ g per 100 g}$$

of deionized starting mixture.

TABLE 1

| Components (% by weight) | A | B | C |
|---|---|---|---|
| H$_2$O | 0.9 | 2.5 | 1.5 |
| HCOONa | 3.4 | 59 ppm | 60 ppm |
| HCOOH | 0.1 | 0.02 | 1.3 |
| Free CH$_2$O | 0.7 | 0.13 | 1.6 |
| Isobutanol | 8.8 | 0.03 | — |
| By-products having the composition indicated on Table 2 | 86.1 | 97.3 | 95.6 |

TABLE 2

| Components (% by weight) | A | B | C |
|---|---|---|---|
| PE(*) monomethyl ether | 0.8 | 2.4 | 0.6 |
| PE cyclic formal | 23.2 | 22.4 | 22.4 |
| mixed CH$_3$OH/PE formal | 4.9 | 8.2 | 3.5 |
| PE dimethylether | 0.9 | 1.5 | 0.7 |
| Pentaerythritol | 12.3 | 20.6 | 18.8 |
| Dipentaerythritol | 2.1 | 1.8 | 1.5 |
| PE linear formal | 0.5 | — | 1.5 |
| Other formals | 12.3 | 7.8 | 14.5 |
| Not identified organic compounds | 43.0 | 35.3 | 36.5 |

(*)PE = pentaerythritol.

EXAMPLE 2

441 g of the mixture marked A on Table 1 were brought into contact with 147 grams of methanol, in the presence of 22 g of 98% H$_2$SO$_4$, according to the operating conditions followed in the preceding example; the temperature passed from 71° to 88° C. in the flask and, in the head of the column, it rose from 40° to 64° C. Thereby were gathered 110 g of a distillate containing (% by weight):

| H$_2$O | 0.3% | CH$_3$O—CH$_2$—OCH$_3$ | 47.9% |
|---|---|---|---|
| CH$_3$OCH$_3$ | 0.2% | CH$_3$OH | 39.3% |
| HCOO—CH$_3$ | 12.3% | | |

From the residual bottoms in the flask, while operating as in example 1, were extracted 121 g of crystals containing 86.0% by example of PE and 8% by weight of sodium sulphate, which corresponds to 23.6 g of PE every 100 g of starting mixture A. It must be pointed out that originally the free pentaerythritol was equal only to $$12.3 \times \frac{86.1}{100} = 10.6 \text{ g}/100 \text{ g}$$

of starting mixture A.

EXAMPLE 3

399 g of the deionized mixture indicated on Table 1 as mixture B, were poured into a flask containing 210 g of isobutanol, in the presence of 12 g of 98% H$_2$SO$_4$. This reaction mixture was heated for 3 hours by total reflux, thereby stabilizing the temperature around 103° C. The mixture was then cooled down to room temperature, filtered under pressure and finally washed with 100 g of methanol, thereby obtaining 121 g of crystals containing 94.5% by weight of PE, that is 28.7 g of PE per 100 g of starting mixture B, against the 20 grams of free PE that were originally present in each 100 g of mixture B. It should be noted that considerably lower yield with respect to the yield that can be obtained using methanol.

EXAMPLE 4

396 g of the de-ionized mixture indicated with B on Table 1, were brought into contact with 297 g of 1,3-propylene glycol, in the presence of 6 g of 98% $H_2SO_4$, operating as in example 1, under an absolute pressure of 80 mmHg and with a reflux ratio of 20:1, whereby the temperature in the flask rose from 110° to 130° C., while in the head of the rectifying column the temperature rose from 25° to 35° C. After 2.5 hours were gathered 155 g of a distillate containing (% by weight):

| $H_2O$ | 2.5% by weight | 1,3-dioxane | 82.4% |
|---|---|---|---|
| $CH_3OH$ | 11.7% by weight | other compounds | 3.4%. |

The reaction mixture was thereupon cooled down to room temperature, suspended in 1,000 g of methanol for about half an hour and finally filtered under pressure. The crystals thus obtained were then suspended in 100 g of methanol, filtered again and then washed with further 100 g of methanol; thereby were obtained 203 g of crystals containing 97% by weight of pentaerythritol, that is, 49.7 g of PE/100 g of initial de-ionized mixture, against the 20 g that were originally present.

EXAMPLE 5

800 g of the mixture indicated on Table 1 by C, were brought into contact, in a carbon steel autoclave with thermostatically controlled heating and fitted with a stirrer, with 325 g of $CH_3OH$, and the whole was then brought up to a temperature of 87° C.; the pressure rose to 1.7 atm. (absolute). The mixture was thereupon additioned with 25 g of $H_2SO_4$ at a 98% by weight concentration, dissolved in 100 g of methanol. During the first 15 minutes, an autogenous and gradual rise in pressure up to 2.5 absolute atmospheres was observed. At this point one started to exhaust the vapors that had formed during this first part of the reaction, which vapors contained mainly methylal and methanol, and 760 g/hour of liquid methanol, equal to about the methanol removed in the vapor phase, was fed as a reintegration into the reactor, whereby the pressure rose abruptly again to the level of 1.3 absolute atmospheres. During the test the temperature was kept at 87° C.

2.25 hours after the addition of sulphuric acid, the mixture was rapidly cooled down to room temperature, discharged from the autoclave and then filtered under pressure. The crystals thus obtained were then washed with 200 g of methanol. After drying in an oven, were obtained 283 g of crystals containing 94.0% by weight of pentaerythritol, which corresponds to 33.3 g of PE/100 g of initial mixture C (deionized mixture). Originally the free pentaerythritol was equal only to $$18.8 \times \frac{95.6}{100} \text{ 18 g per 100 g}$$

of initial deionized mixture.

EXAMPLE 6

300 g of the mixture indicated as C in Table 1, were mixed with 70 g of methanol and with 280 g of a strongly acidic cation exchange resin (KASTEL C-331-P, manufactured by Montedison, S.p.A.). The procedure of Example 1 was repeated except for the periodic liquid reintegration of methanol, in order to keep constant its content in the reaction mixture. The reaction was carried out for 9 hours with a reaction temperature of 72° C. (±2° C.) and with a head distillation temperature of from 50° to 63.5° C. After 6 hours and 12 minutes, 156 grams of distillate were obtained. The composition of the distillate is given in the following Table (weight percent):

| $H_2O$ | 0.45 | $CH_3OCH_2OCH_3$ | 36.80 |
|---|---|---|---|
| $CH_3OCH_3$ | 0.45 | $CH_3OH$ | 61.75 |
| $HCOOCH_3$ | 0.55 | | |

A second distillate, collected between the first one and the end of the distillation, weighed 57 g, and contained (weight percent):

| $H_2O$ | 0.30 | $CH_3OCH_2OCH_3$ | 10.62 |
|---|---|---|---|
| $CH_3OCH_3$ | 0.50 | $CH_3OH$ | 88.58 |
| $HCOOCH_3$ | <0.05 | | |

At the end of the reaction, the reactor and its contents were cooled down to a temperature of 25° C. and said contents were mixed together with 100 g of methanol. The ion exchanger was then removed from the reaction mixture by wet screening on a 60 mesh steel sieve, and then washed with 200 grams of methanol; the latter one and the slurry not retained by the screening, were mixed together and filtered under pressure. The cake was then washed with 100 g of methanol and then dried in an oven, whereby there were obtained 140 g of a solid whose pentaerythritol content was found to be 97.5% by weight. This means that 45.5 parts of pentaerythritol were obtained from 100 parts of starting mixture C. Originally the "free" pentaerythritol was only $$18.8 \times \frac{95.6}{100} = 18 \text{ parts by 100 parts}$$

of starting mixture C.

What is claimed is:

1. A method for recovering pentaerythritol from a residual mixture of the synthesis of pentaerythritol from acetaldehyde and formaldehyde containing, besides other by-products, at least 20% by weight of formals, which method is characterized in that said formals are transacetalized by contacting the residual mixture containing them, in a liquid medium and in the presence of an acid selected from the group consisting of sulphuric, phosphoric paratoluene-sulphonic acids and the cation-exchange resins, with a saturated aliphatic alcohol selected from the group consisting of methanol, ethylene glycol and 1,3-propylene glycol, the amount of water in the transacetalization reacting mixture being equal to or lower than 10% by weight.

2. The method of claim 1, in which the amount of water in the transacetalization reacting mixture is about 5% by weight.

3. The method of claim 1, in which the residual mixture containing at least 20% by weight of formals is contacted, in the liquid medium and in the presence of the acid, with the saturated aliphatic alcohol at a temperature higher than 60° C. and for a period of time longer than 15 minutes.

4. The method of claim 1, in which the residual mixture containing at least 20% by weight of formals is contacted, in the liquid medium and in the presence of the acid, with the saturated aliphatic alcohol at a temperature of about 70° C. to about 130° C.

5. The method of claim 1, in which the residual mixture containing at least 20% by weight of formals is contacted, in the liquid medium and in the presence of the acid, with the saturated aliphatic alcohol at a temperature of about 70° C. to about 130° C. for a period of time longer than 15 minutes, and the amount of water in the transacetalization reacting mixture is equal to or lower than 5% by weight.

6. The method of claim 4 in which the residual mixture containing at least 20% by weight of formals is contacted, in the liquid medium and in the presence of the acid, with the saturated aliphatic alcohol for a period of time of 0.5 to 5 hours, and the amount of water in the transacetalization reacting mixture is about 5% by weight or less.

7. The method of claim 6 in which the formals in the residual mixture containing at least 20% by weight of formals are transacetalized by contacting said residual mixture, in the liquid medium and in presence of the acid, with the saturated aliphatic alcohol under a pressure between atmospheric pressure and 5 absolute atmospheres.

8. The method of claim 1 in which the formals in the residual mixture containing at least 20% by weight of formals are transacetalized by contacting the residual mixture, in the liquid medium and in the presence of sulphuric, phosphoric or para-toluene sulphonic acid, or of a cation exchange resin, with methanol, ethylene glycol or 1,3-propylene glycol, at a temperature of higher than 60° C., for a period of time longer than 15 minutes, and under a pressure between atmospheric pressure and 5 absolute atmospheres.

9. The process of claim 8 in which the residual mixture containing at least 20% by weight of formals is contacted, in the liquid medium and in the presence of the acid, with the saturated alcohol for from 0.5 to 3 hours.

10. A method for the recovery of pentaerythritol from a residual mixture of the synthesis of pentaerythritol, said residue containing, besides other by-products, at least 20% by weight of formals, said method being characterized in that formals contained in said residual mixture are transacetalized by contacting the residual mixture, in a liquid medium and in the presence of at least the stoichiometrically equivalent amount of sulphuric, phosphoric or para-toluene sulphonic acid or of a cation exchange resin, with methanol, ethylene glycol or 1,3-propylene glycol, at a temperature of 70° to 130° C., for from 0.5 to 3 hours, and under a pressure of between atmospheric pressure and 5 absolute atmospheres, the amount of water in the transacetalization reacting mixture being not more than about 5% by weight.

11. The method of claim 10 in which the residual mixture containing at least 20% by weight of formals is contacted, in the liquid medium and in the presence of sulphuric acid in an amount of from 0.5 to 10% by weight based on the weight of the total reacting mixture.

12. The method of claim 10 in which the residual mixture containing at least 20% by weight of formals is contacted, in the liquid medium and in the presence of the acid, with the saturated aliphatic alcohol in a molar ratio of the alcohol to the residual mixture of 0.2 to 3.0.

13. The method of claim 12, in which the molar ratio of the alcohol to residual mixture is 0.25 to 1.0.

14. The method of claim 12, in which the residual mixture containing at least 20% by weight of formals is contacted, in the liquid medium and in presence of the acid, with methanol, at a temperature of 70° C. to 100° C.

* * * * *